United States Patent [19]

Lewin

[11] 4,138,464
[45] * Feb. 6, 1979

[54] BLOOD OXYGENATOR WITH INTEGRAL HEAT EXCHANGER

[76] Inventor: John E. Lewin, 13462 Eton Pl., Santa Ana, Calif. 92705

[*] Notice: The portion of the term of this patent subsequent to Dec. 27, 1994, has been disclaimed.

[21] Appl. No.: 863,988

[22] Filed: Dec. 23, 1977

Related U.S. Application Data

[63] Continuation-in-part of Ser. No. 685,020, May 10, 1976, Pat. No. 4,065,264.

[51] Int. Cl.² .............................................. A61M 1/03
[52] U.S. Cl. ................................. 422/46; 128/DIG. 3; 165/133; 422/47
[58] Field of Search ................. 23/258.5 R, 258.5 BH, 23/258.5 MH, 258.5 A, 258.5 B; 165/1, 163, 184, 133; 128/399, 400, DIG. 3, 214 A

[56] References Cited

U.S. PATENT DOCUMENTS

| | | |
|---|---|---|
| 2,374,609 | 4/1945 | McCallum ........................ 165/184 X |
| 2,934,067 | 4/1960 | Calvin ........................... 23/258.5 BH |
| 2,965,819 | 12/1960 | Rosenbaum ................... 165/133 UX |
| 3,015,355 | 1/1962 | Humphrey ......................... 29/423 X |
| 3,291,568 | 12/1966 | Sautter ......................... 23/258.5 BH |
| 3,437,450 | 4/1969 | Greenwood ..................... 23/258.5 A |
| 3,468,631 | 9/1969 | Raible et al. ................. 23/258.5 BH |
| 3,578,411 | 5/1971 | Bentley et al. ............... 23/258.5 BH |
| 3,730,229 | 5/1973 | D'Onofrio ....................... 165/184 X |
| 3,731,731 | 5/1973 | Kyvsgaard ............................ 165/46 |
| 3,746,084 | 7/1973 | Ostbo .................................. 165/163 |
| 3,769,162 | 10/1973 | Brumfield .................... 23/258.5 BH |
| 3,802,499 | 4/1974 | Garcea ................................ 165/163 |
| 3,898,045 | 8/1975 | Bowley ........................ 23/258.5 BH |
| 4,065,264 | 12/1977 | Lewin ........................... 23/258.5 BH |
| 4,067,696 | 1/1978 | Curtis .............................. 23/258.5 B |
| 4,073,622 | 2/1978 | Luppi ........................... 23/258.5 BH |

FOREIGN PATENT DOCUMENTS

| | | | |
|---|---|---|---|
| 567997 | 3/1945 | United Kingdom ...................... 165/163 |
| 870271 | 6/1961 | United Kingdom ...................... 165/163 |
| 1144448 | 3/1969 | United Kingdom ...................... 165/184 |

*Primary Examiner*—Barry S. Richman

[57] ABSTRACT

A blood oxygenator includes a heat exchanger wherein heat transfer fluid flows through an aluminum tube having an intergral, substantially continuous hollow helical rib along its length providing a substantially continuous helical flute. The tube is positioned within a chamber connected in an extracorporeal blood circuit such that the blood is caused to flow over the anodized exterior surface of the helically ribbed tube. In the preferred embodiment, the blood flows through a plurality of continuous, restricted area flow paths offering substantially uniform flow impedance to the blood, these restricted flow paths being provided by forming the helically ribbed tube in a helical configuration mounted between an inner cylindrical column and an outer cylindrical shell such that the blood is caused to flow through the plural paths of restricted cross-sectional area provided by the helical flute. In one embodiment, the heat exchanger tube and blood chamber are formed as an independent unit adapted for use in the desired location of an extracorporeal blood circuit. In the other embodiments, the heat exchanger is formed integral with a blood oxygenator in which oxygen is absorbed into the blood and carbon dioxide is released therefrom.

9 Claims, 15 Drawing Figures

FIG. 8.
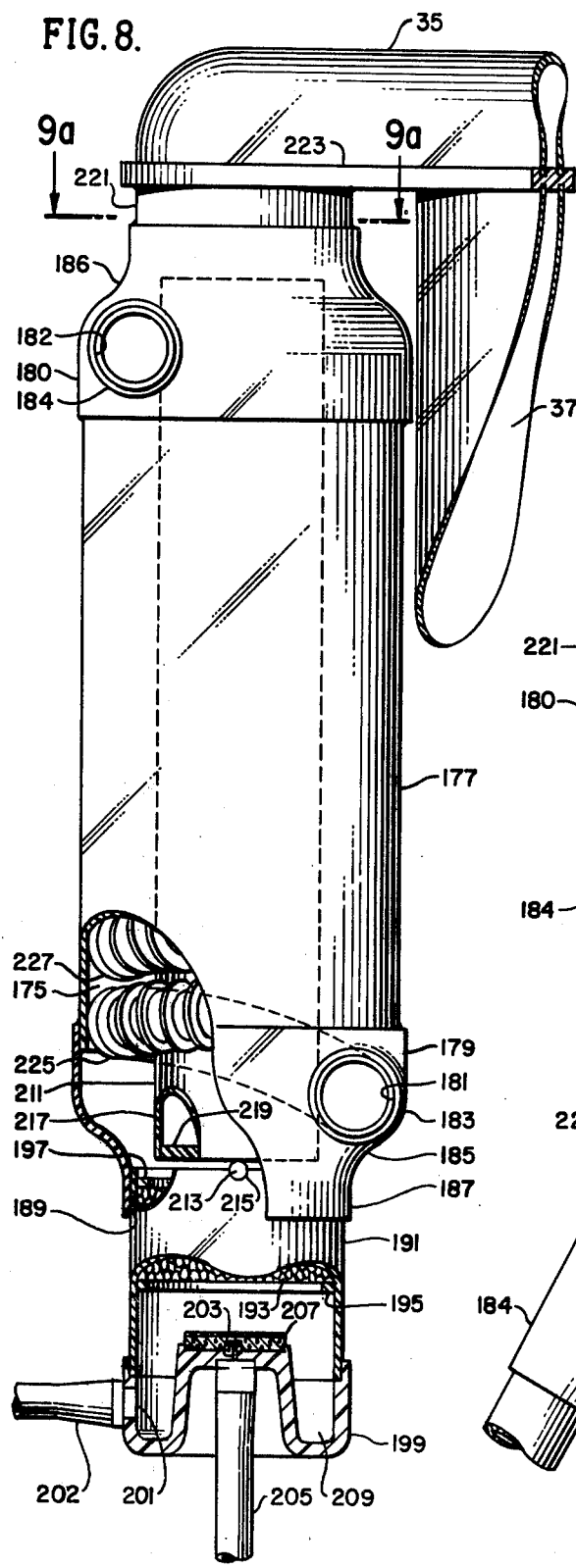
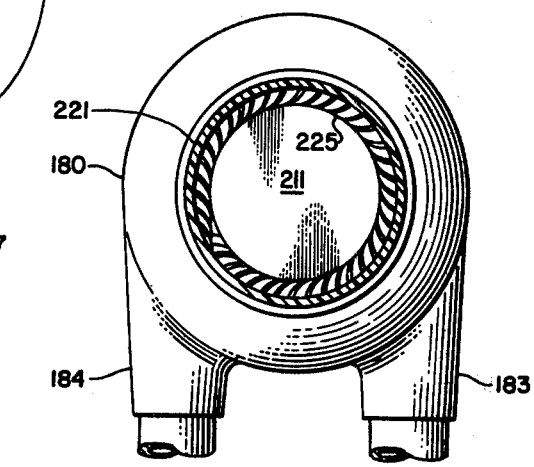
FIG. 9a.
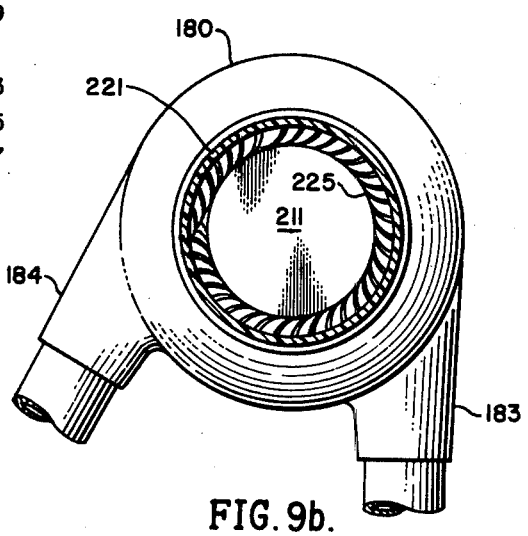
FIG. 9b.

BLOOD OXYGENATOR WITH INTEGRAL HEAT EXCHANGER

CROSS REFERENCE TO RELATED APPLICATION

This is a Continuation-In-Part of Application, Ser. No. 685,020, filed May 10, 1976 now U.S. Pat. No. 4,065,264 issued Dec. 27, 1977.

BACKGROUND OF THE INVENTION

Extracorporeal circulation is and has been a routine procedure in the operating room for several years. An important component in the extracorporeal blood circuit is a heat exchanger used to lower the temperature of the blood prior to and during a surgical procedure and subsequently rewarm the blood to normal body temperature. The cooled blood induces a hypothermia which substantially reduces the oxygen consumption of the patient. The published literature indicates that the oxygen demand of the patient is decreased to about one-half at 30° C., one-third at 25° C. and one-fifth at 20° C. Light (33 to 35° C.), moderate (26 to 32° C.), and deep (20° C. and below) hypothermia are commonly used in clinical practice. Hypothermia is used to protect the vital organs including the kidneys, heart, brain and liver during operative procedures which require interrupting or decreasing the perfusion.

A number of different structural configurations for heat exchangers have been used in the extracorporeal blood circuit including hollow metal coils, cylinders and plates through which a heat transfer fluid (typically water) is circulated. A survey of a number of different type of heat exchangers used in extracorporeal circulation is included in the book entitled "Heart-Lung Bypass" by Pierre M. Galletti, M.D. et al, pages 165 to 170.

Notwithstanding the plurality of different types of heat exchanger configurations which have been used in the past, there remains a need for a safe highly efficient heat exchanger design which is simple to use and yet inexpensive enough to be manufactured as a disposable item. Thus, it is important that there not be any leakage of the heat transfer fluid into the blood. This fluid is typically circulating water flowing from plumbing fixtures located in the operating room. Certain of the heat exchangers commonly used today for clinical bypass operations have an upper pressure limit which is sometimes lower than the water pressures obtainable in the hospital operating room. The person who connects up the heat exchanger must therefore be very careful to never apply the full force of the water pressure through such a heat exchanger. Failing to take this precaution, or an unexpected increase in water pressure, could cause a rupture within the heat exchanger resulting in contamination of the blood flowing through the blood oxygenator.

It is also important that the heat exchanger have a high performance factor in order to reduce to a minimum the time required to lower the temperature to induce hypothermia and subsequently raise the blood temperature to normal. Some physiological degradation of the blood occurs after a patient is connected only a few hours to any of the bubble oxygenators presently in use. Therefore, time saved in cooling and rewarming the blood is of direct benefit to the patient and also gives the surgeon additional time to conduct the surgical procedure if necessary. Heretofore, stainless steel tubing has often been used in blood environments as a heat exchange element because it is biologically compatible with human blood. However, heat exchangers made with stainless steel tubing are very expensive and are not economically suited for a throw away disposable unit.

SUMMARY OF THE INVENTION

The present invention relates to a heat exchanger for an extracorporeal blood circuit formed by an aluminum tube having one or more integral hollow ribs along its length and having substantially its entire exterior surface electrolytically oxidized to form a hard anodized coating. This tube in turn is formed in an overall helical configuration and mounted between an inner cylindrical column extending within the helically configured tube and an outer cylindrical shell. Both the column and the shell are sized such that peripheral portions of the rib are in contact with or are closely proximate to the exterior wall of the column and the interior wall of the cylindrical shell. The method employed for regulating the temperature of blood using this type of heat exchange element involves flowing a heat transfer fluid through the tube and hollow rib and flowing the blood in a counterflow direction over the exterior surface of the ribbed tube. The combination of the rib and the contacting surfaces of the cylinder and chamber confine the flow of blood substantially within paths of restricted area and extended length provided by the hollow ribbing.

The heat exchanger of the present invention enjoys several significant advantages. Thus, its performance factor is very high due to the long residence time of the blood, the high conductivity of the heat exchange tube, the direct contact of the blood with the hard anodized surface, the counterflow operation, and high flow rate of the heat transfer fluid through the ribbed tube.

Heat exchangers constructed in accordance with the present invention have the reliability necessary for routine use in open heart surgery and other procedures utilizing extracorporeal circulation. The anodized metal heat transfer fluid tube is an integral member which may be completely tested, both before and after assembly into the blood chamber, for leaks under substantially higher fluid pressures than are ever encountered in an operating room environment. The integral nature of the heat exchange tube also provides an important advantage in that only the ends of the tube pass through the wall of the blood carrying chamber, thus minimizing the number of openings in the chamber which must be hermetically sealed. Moreover, no connections need to be made to the tube within the blood chamber since a heat transfer fluid inlet and heat transfer fluid outlet are provided by the ends of the tube extending out from the chamber. Any leak at the connection of the heat exchanger tube and the fluid supply conduit will merely leak water or other heat transfer fluid external of the blood chamber.

The hollow ribbed heat exchanger tube may be mounted within a blood chamber separate from the blood oxygenator or may be incorporated integral with the blood oxygenator, e.g., in the venous side within the blood-oxygen mixing chamber or in the outlet side within the defoaming chamber. In the embodiments described below in which the heat exchanger is incorporated within the mixing chamber of a bubble oxygenator the flow of the blood and blood foam through the lengthy paths of restricted cross-sectional area contributes to the blood-gas transfer process.

The heat exchangers of this invention are sufficiently economical in terms of material and manufacturing costs so that it is disposed of after use, thus avoiding the problems and cost of sterilization in the hospital. In addition, the heat exchangers constructed in accordance with this invention may be made biologically inactive and compatible with human blood. A significant advantage of this invention is that the anodized exterior surface of the metal heat exchanger is compatible with human blood. Thus, no other coating such as a plastic coating is required over this anodized tube so that the blood may flow directly in contact with this surface and achieve a very high performance factor.

BRIEF DESCRIPTION OF THE DRAWINGS

FIG. 8 is a vertical elevational partial sectional view of another embodiment of a blood oxygenator having an integral heat exchanger constructed in accordance with the present invention;

FIG. 9a is a partially sectional view taken along the line 9—9 of FIG. 8 showing the heat exchanger tube ends in parallel alignment;

FIG. 9b is a partially sectional view taken along the line 9—9 of FIG. 8 showing the heat exchanger tube ends in a non-parallel alignment;

Figures 1, 2:
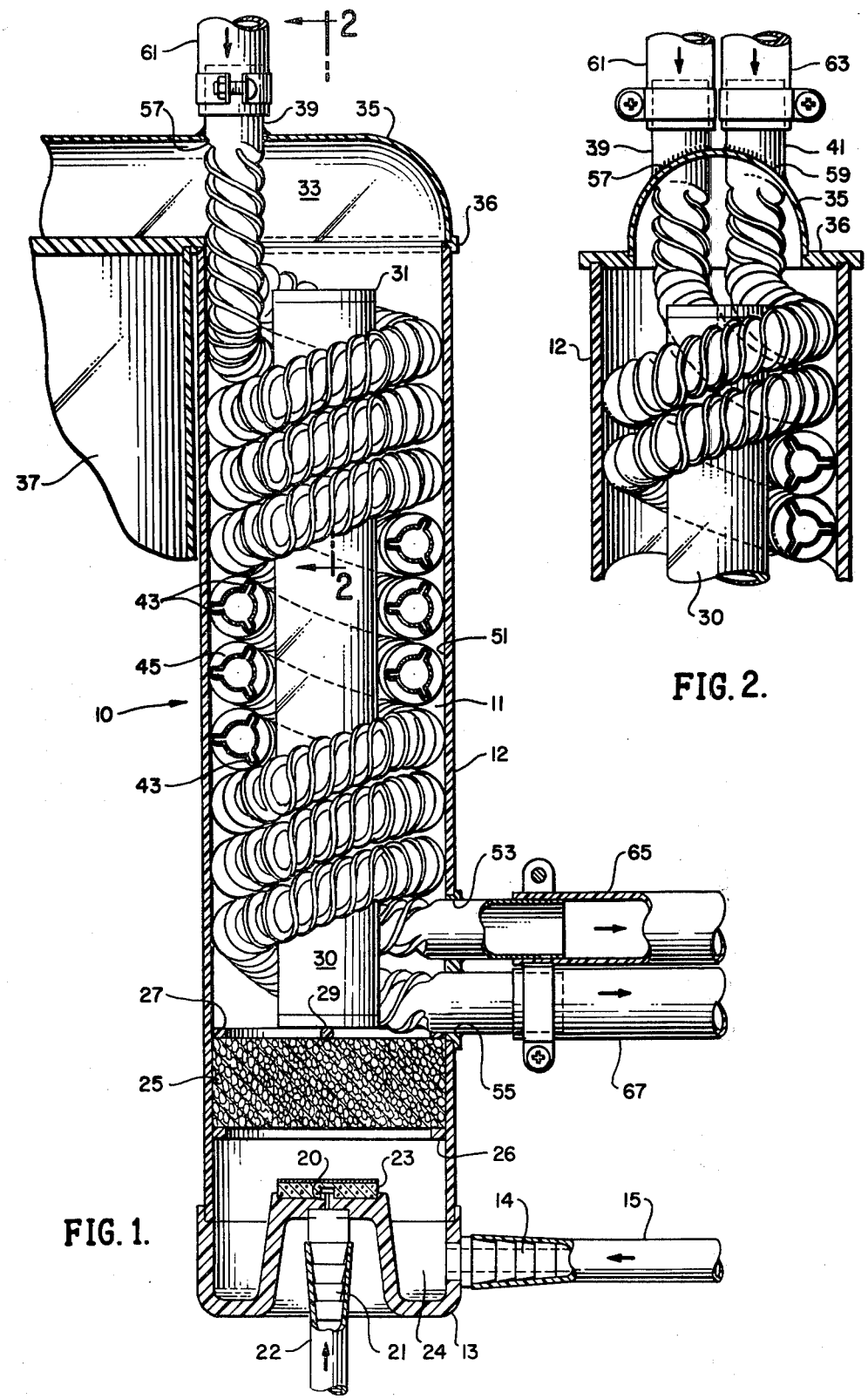
FIG. 1 is a vertical elevational partial sectional view of a blood oxygenator having an integral heat exchanger constructed in accordance with the present invention.
FIG. 2 is a partially sectional view taken along the line 2—2 of FIG. 1.

DETAILED DESCRIPTION OF THE EMBODIMENT OF FIGS. 1 and 2

Referring to FIGS. 1 and 2, a blood oxygenator 10 is shown incorporating a heat exchanger in accordance with this invention. In this first embodiment as well as the other embodiments described below and illustrated in FIGS. 3, 4, and 8 through 14 the blood oxygenator 10 is shown constructed in accordance with the invention disclosed and claimed in application Ser. No. 655,039, filed Feb. 3, 1976 by Robert M. Curtis, entitled BLOOD OXYGENATOR and assigned to Shiley Laboratories, Inc., the assignee of the present invention. The bubble oxygenator chamber 11 is formed by a cylindrical shell 12 having its lower end closed off by a multi-port end cap 13. In the outer wall of the end cap 13 are formed one or more blood inlet ports, one such port 14 being connected to the extracorporeal blood circuit by a flexible venous blood conduit 15. In the center of the cap 13 and extending through the wall thereof is an oxygen inlet port 20 including an outwardly extending ridged connector 21 for attachment to a flexible oxygen line 22. The oxygen entering the inlet port 20 is caused to form a plurality of oxygen bubbles by means of a sparger 23. These bubbles flow through the venous blood entering the annular trough 24 formed by the end cap 13 and the blood and oxygen mixture flow upwardly through a three-dimensional, open cellular mixing material 25 supported above the sparger 23 within the chamber 11 by a pair of annular retaining rings 26 and 27. The mixing material 25 is formed as a cylinder so as to completely fill the cross-sectional space within the cylindrical shell 12 between the annular retaining rings 26 and 27.

A column 30 is coaxially mounted within the upright cylindrical shell 12 and supported by a horizontal rod 29 formed as an integral cross brace of the annular retaining ring 27. Both ends of the column 30 are hermetically sealed by caps 31.

The top of the chamber 11 is open. The arterialized blood in the form of liquid blood and blood foam rises through this opening and is contained in a channel 33 formed by a generally half cylindrical shell 35 secured to a flat cover plate 36. As described in the co-pending application of Robert M. Curtis, supra, the channel 33 leads to a defoamer chamber 37 wherein the foam is collapsed and the arterialized whole blood collected and returned to the extracorporeal blood circuits.

The heat exchanger comprises a pair of helically ribbed, heat transfer fluid tubes 39 and 41. As shown, the hollow ribs 43 on these tubes have a triple helix configuration and provide a continuous series of helical flutes 45. These helically ribbed tubes 39 and 41 are advantageously constructed from a thin wall tube of metal. Methods and apparatus for manufacturing such helically ribbed tubes are described in U.S. Pat. Nos. RE24,783 and 3,015,355.

The heat transfer fluid tubes 39 and 41 are advantageously formed of a continuous aluminum tube whose exterior surface has been electrolytically oxidized (anodized) to produce a heavy surface oxide coating to resist corrosion. The result is an inexpensive, reliable, and durable heat exchange element which achieves an efficient transfer of heat from the blood to the heat transfer fluid, and which is compatible with human blood.

The anodization of aluminum is well known, and various techniques may be employed. It has been found to be most advantageous to anodize the aluminum tube in the present invention with what is known as a "hard coating," which is produced electrolytically in a sulfuric acid bath, as per Military Specification MIL-A-8625C, as amended.

As shown in FIGS. 1 and 2, the helically ribbed tubes 39 and 41 are formed in a helical configuration and mounted between the central column 30 and the interior wall of the shell 12 such that peripheral portions of the ribs are closely proximate to and advantageously in contact with the exterior surface of the column 30 and the interior wall 51 of the bubble oxygen chamber 11. One end of each of the respective tubes 39 and 41 passes through hermetically sealed openings 53 and 55 formed in the bottom of the chamber 11 and the opposite ends of the tubes extend through hermetically sealed openings 57 and 59 formed in the cylindrical shell 35. Urethane glue provides and effective sealant between the outer surface of the hard anodized tube and the chamber 11 and shell 35 formed of polycarbonate plastic.

Shell 12 is advantageously extruded from polycarbonate plastic and includes a longitudinal slit (not shown) such that the shell may be opened up during manufacture to accept the helically ribbed tubes 39 and 41. After these tubes and the inner column 30 are mounted in place, the slit edges of the shell and bonded together by ethylene dichloride.

Flexible conduits 61 and 63 are clamped to the upper ends of tubes 39 and 41 for supplying a heat transfer fluid, typically water under pressure, at the desired temperature. The lower ends of the ribbed tubes 39 and 41 are connected through flexible conduits 65 and 67 to a drain. In this manner, the flow of heat transfer fluid is opposite to that of the flow of the blood in the oxygenator chamber 11 to produce a counterflow-type heat exchanger.

Since the embodiment of FIGS. 1 and 2 has many features and advantages in common with the other embodiments described below, such features and advantages are described in detail hereinafter. A primary distinguishing feature of the embodiment of FIGS. 1 and 2 is the use of dual heat exchanger tubes 39 and 41. The heat transfer performance of a heat exchanger is related to the flow rate of the heat transfer fluid. Although the single tube heat exchanger shown in the embodiments described hereinafter has been found to have a most satisfactory performance in all operating room environments tested to date, the double tube embodiment of FIGS. 1 and 2 would be particularly useful if only very low flow rates of heat transfer fluid were available during the extracorporeal procedure.

Figure 3:
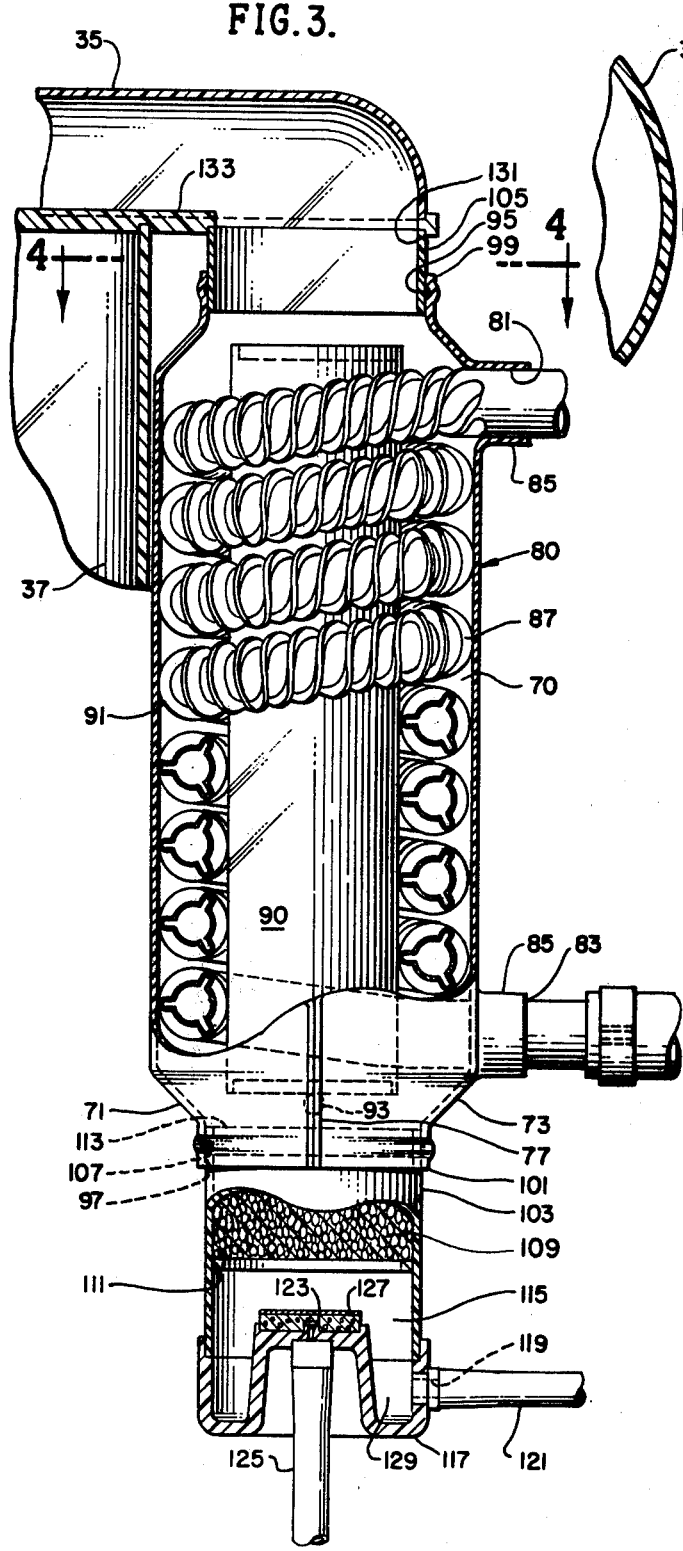
FIG. 3 is a vertical elevational partial sectional view of another embodiment of a blood oxygenator having an integral heat exchanger constructed in accordance with the present invention.
Figure 4:
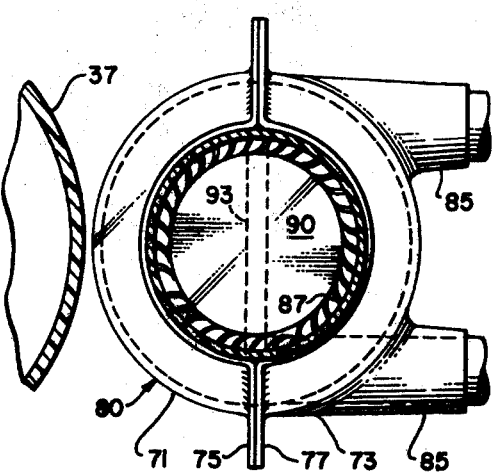
FIG. 4 is a partially sectional view taken along the line 4—4 of FIG. 3.

DETAILED DESCRIPTION OF THE EMBODIMENT OF FIGS. 3 and 4

Another embodiment of a blood oxygenator incorporating an integral heat exchanger in accordance with this invention is shown in FIGS. 3 and 4. In this embodiment, the bubble oxygenating chamber 70 is formed by a pair of mating plastic shells 71 and 73, each including a flat peripheral flange 75 and 77 which may be joined together to form a complete cylindrical shell 80. Shell halves 71 and 73 are advantageously formed by vacuum forming or injection molding polycarbonate plastic.

Cylindrical shell 80 includes an upper side opening 81 and a lower side opening 83 each having an integral outwardly extending cylindrical boss 85 through which extend the respective ends of a single helically ribbed heat transfer fluid tube 87. The inside wall of these extending cylindrical bosses 85 and the proximate exterior surface of the heat exchanger tube 87 are bonded together to effect a hermetic seal. Ethylene dichloride forms an excellent bond between shell havles formed of polycarbonate plastic.

A particular advantage of the construction shown in FIGS. 3 and 4 is that the heat coil 87 may be easily assembled within the chamber 70. When the ribbed tube 87 is formed into a helical configuration, it has a tendency to open up, thereby resulting in a certain amount of sliding frictional contact with the inside walls of the chamber 70 and the exterior walls of the column 90 when mounted in a unitary cylindrical shell such as shown in FIGS. 1 and 2 at 12. In the embodiment of FIGS. 3 and 4, the interior column 90 is inserted within the helically formed ribbed tube 87 and both members placed in the shell half 73 such that the two ends of heat exchange tube 87 extend through the openings 81 and 83. The mating shell half 71 is placed over the heat exchanger tube 87 and the mating flanges 75 and 77 bonded together to provide a completely sealed cylindrical shell unit 80. As in the previously described embodiment, the peripheral portions of the ribs 91 of the tube 87 advantageously contact both the interior wall of chamber 70 and the exterior wall of the column 90.

A plastic rod 93 or other convenient means is affixed to the opposite portions of one or both of the shell halves 71 and 73 for supporting the interior column 90 in a predetermined position.

The mating shells 71 and 73 are necked in at their bottom and top to form respective openings 95 and 97 having cylindrical flanges 99 and 101. Flange 101 snugly mates with the outside diameter of a cylindrical member 103 on the bottom and a cylindrical member 105 on the top respectively. As shown, a small annular groove 107 may be formed in each of the flanges 99 and 101 to accommodate an additional amount of bonding material for providing a hermetic seal between the blood chamber 80 and the cylinders 103 and 105.

Three dimensional, open cellular mixing material 109 is supported within cylinder 103 by a pair of annular rings 111 and 113 attached to the inner wall of cylinder 103. This mixing material completely fills the cross-sectional interior of the chamber 115 along the length of the mixing material.

An end cap 117 is secured to and closes off the bottom of cylinder 103. This cap includes one or more blood inlet ports, one such port 119 being connected to the extracorporeal blood circuit by a flexible venous blood conduit 121. In the center of the cap 117 and extending through the wall thereof is an oxygen inlet port 123 attached to a flexible oxygen line 125. The oxygen entering the inlet port 123 is caused to form a plurality of oxygen bubbles by means of a sparger 127. These bubbles flow through the venous blood entering the annular trough 129 formed by the end cap 117.

The upper cylinder 105 is secured within an opening 131 formed in a flat cover plate 133. The arterialized whole blood rises through this opening and is contained in a channel formed by the cylindrical shell 35 through which it is passed to a defoamer chamber 37 a described in the copending application of Robert M. Curtis, supra.

Figure 5:
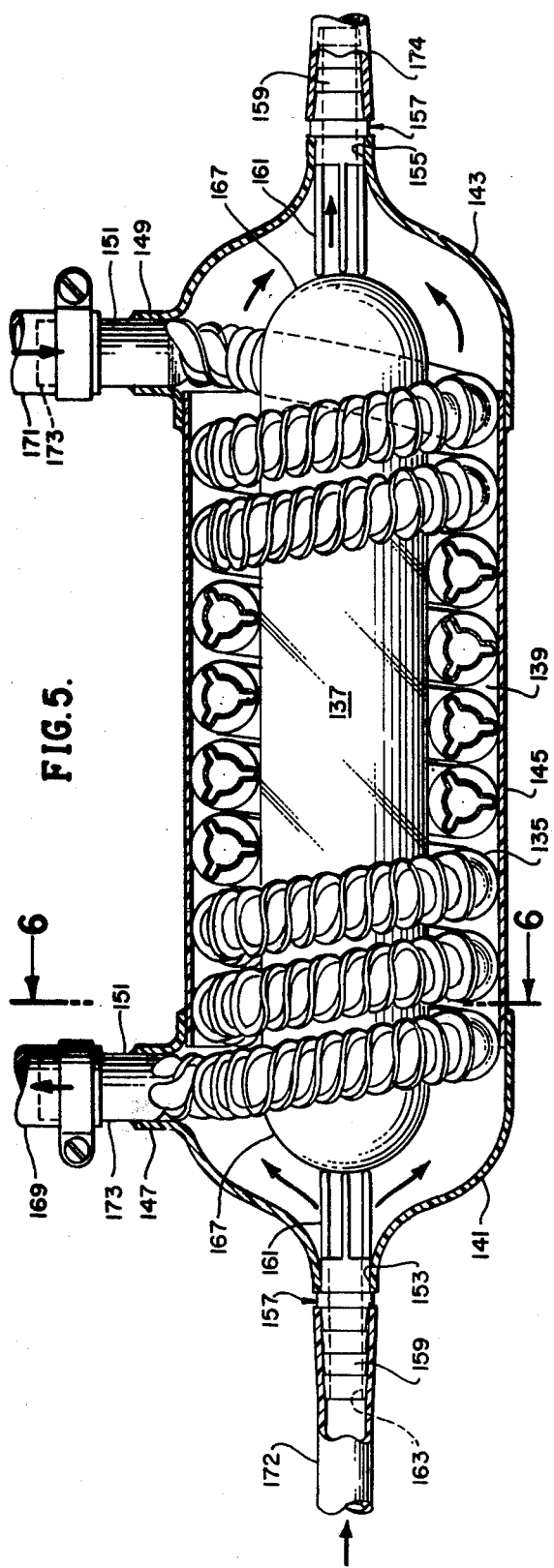
FIG. 5 is a vertical elevational partially sectional view of a heat exchanger constructed in accordance with the present invention for use as a separate component in an extracorporeal blood circuit.
Figure 7:
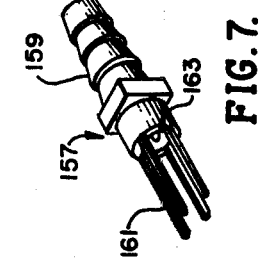
FIG. 7 is a perspective view of the port member providing a fluid conduit, a ridged connector and rods for positioning the centrally located column shown in FIG. 5.
Figure 6:
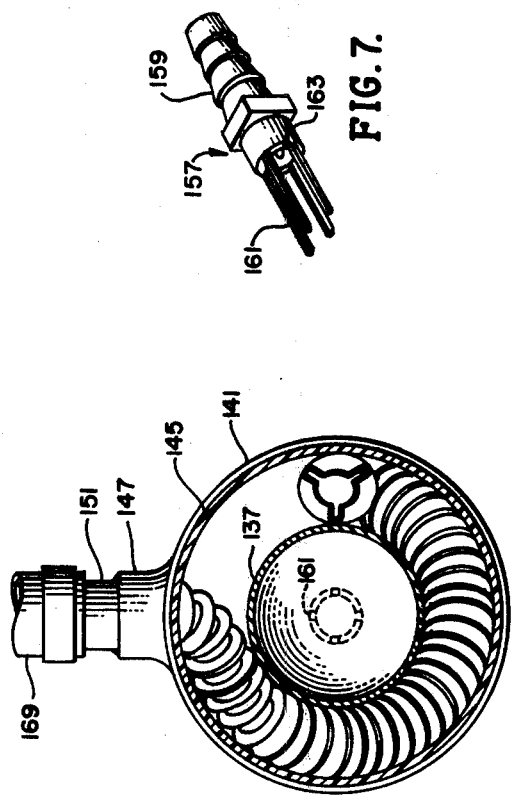
FIG. 6 is a partially sectional view taken along the line 6—6 of FIG. 5.
Figure 10:
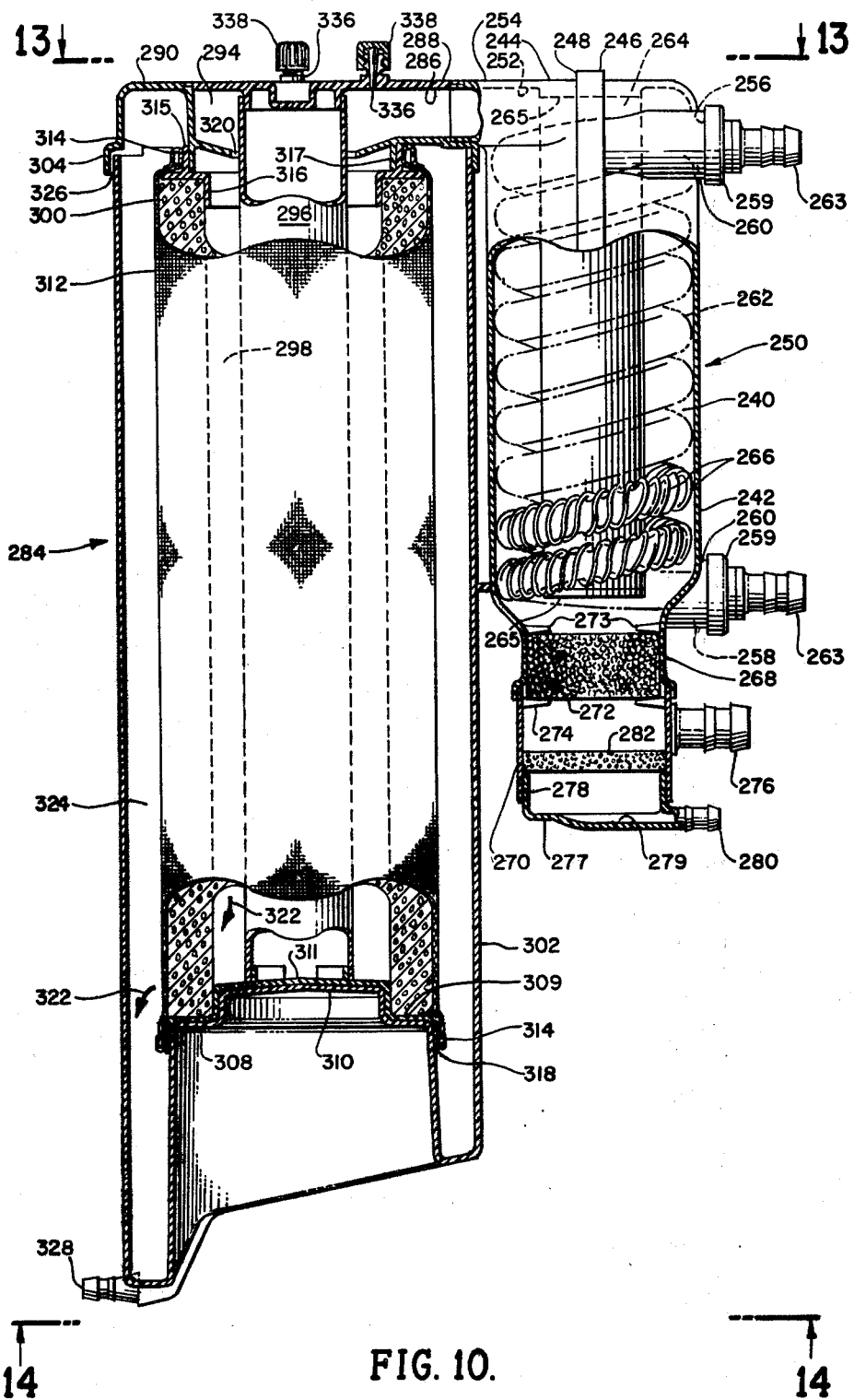
FIG. 10 is a vertical elevational sectional view of the preferred embodiment of a blood oxygenator having an integral heat exchanger constructed in accordance with the present invention.
Figures 11, 12:
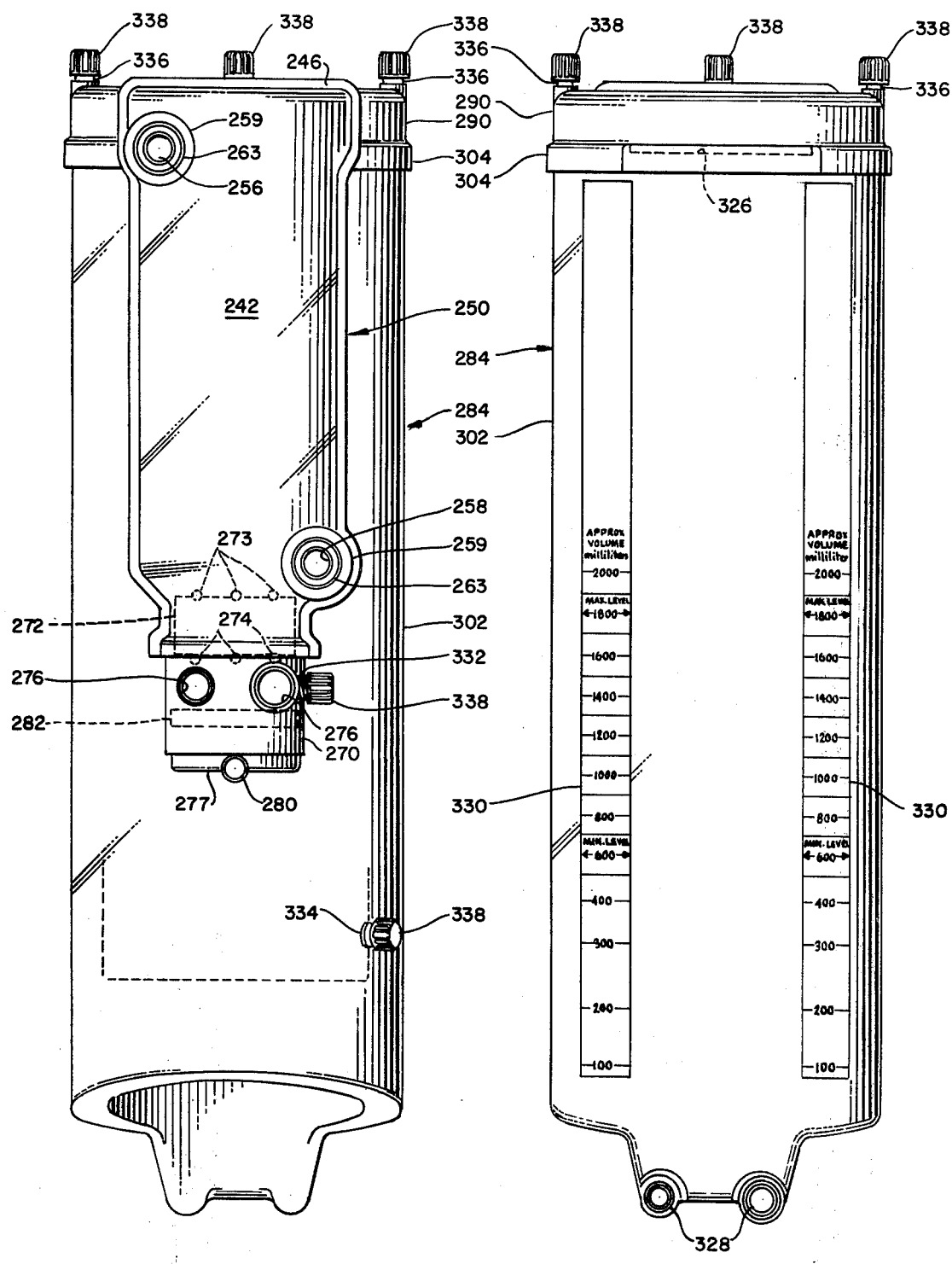
FIG. 11 is a front elevational view of the preferred embodiment of a blood oxygenator having an integral heat exchanger constructed in accordance with the present invention.
FIG. 12 is a rear elevational view of the preferred embodiment of a blood oxygenator having an integral heat exchanger constructed in accordance with the present invention.

DETAILED DESCRIPTION OF THE EMBODIMENT OF FIGS. 5, 6 and 7

Although the invention has been described hereinabove as integral with a blood oxygenator, the heat exchanger of this invention may be incorporated in a separate unit to be used elsewhere in extracorporeal blood circuits. Referring now to FIGS. 5, 6, and 7, the same type of helically ribbed heat transfer fluid tube 135 is mounted in a spiral configuration between an interior cylindrical column 137 and within a cylindrical chamber 139. Advantageously, peripheral portions of the ribs are in contact with the exterior of the centrally located column 137 and the interior wall of the chamber 139. As described above with reference to the embodiment of FIGS. 1 and 2, the cylinder 145 is advantageously slit along its length for facilitating insertion of the heat transfer fluid tube, after which the edges of the slit are bonded together.

Respective end caps 141 and 143 are secured at opposite ends of the cylinder 145, each with a side opening having an integral outwardly extending cylindrical bosses 147 and 149 through which passes one end of the heat exchanger tube 135. A suitable hermetic seal is formed between that portion of the exterior wall 151 of the heat transfer fluid tube 135 and the inside wall of bosses 147 and 149 to prevent any blood leakage. Typically, a suitable adhesive such as urethane glue is used to form a bond between the cylinder 145 and end caps 141 and 143 formed of polycarbonate plastic.

The end cap members 141 and 143 each have a central aperture 153 and 155 concentric with the spirally formed heat exchanger tube 135. In each such aperture, there is mounted a port member 157 having a ridged connector portion 159 extending outwardly from the heat exchanger, four support rods 161 extending inwardly into the heat exchanger, and a through conduit 163 through which blood passes into and out of the heat exchanger. As shown in FIG. 5, the four rods 161 make contact with the peripheral end surface 167 of the centrally located column 137 to retain its ends equidistant from the end caps 141 and 143.

In use, flexible water conduits 169 and 171 are attached as shown to the extending ends 173 of the ribbed heat transfer fluid tube 135, conduit 171 being connected to a suitable source of heat transfer fluid under pressure. A counterflow of blood is introduced into the heat exchanger through a flexible conduit 172 attached to the ridged connector 159. The cooled or heated blood flows out of the heat exchanger through port member 157 into flexible conduit 174 attached to the ridged connector 159.

DETAILED DESCRIPTION OF THE EMBODIMENT OF FIGS. 8, 9a and 9b

Another embodiment of a blood oxygenator incorporating an integral heat exchanger in accordance with this invention is shown in FIGS. 8, 9a and 9b. In this embodiment, the bubble oxygenator chamber 175 is formed by a cylindrical shell 177 having its lower end closed off by an end cap 179 having a side opening 181 having an integrally attached, outwardly extending cylindrical boss 183 formed in its outer wall and a necked-in portion 185 at its bottom including a cylindrical flange 187 surrounding a central aperture 189. This cylindrical flange of the end cap 179 is sized to mate with the external diameter of a cylinder 191 and bonded thereto with a suitable material such as ethylene dichloride. A three-dimensional, open cellular mixing material 193 is supported within cylinder 191 by annular rings 195 on its underside and 197 on its upper surface. As shown, material 193 completely fills the cross-sectional interior of the cylinder 191 along the length of the mixing material.

The bottom of cylinder 191 is closed off by a multiport end cap 199. In the outer wall of the end cap 199 are formed one or more blood inlet ports, one such port 201 being connected to the extracorporeal blood circuit by a flexible venous blood conduit 202. In the center of the cap 199 and extending through the wall thereof is an oxygen inlet port 203. The oxygen entering the inlet port 203 via oxygen line 205 is caused to form a plurality of oxygen bubbles by means of a sparger 207. These bubbles flow through the venous blood entering the annular trough 209 formed by the end cap 199 and the blood and oxygen mixture flow upwardly through the three-dimensional, open cellular mixing material 193 supported above the sparger 207 within the cylinder 191.

An upright column 211 is coaxially mounted within the upright cylindrical shell 177 by a horizontal rod 123 supported in appropriate semicircular slots 215 formed in the top surface of the cylinder 191. Column 211 is advantageously formed by a hollow cylindrical member 217 whose ends are sealed by circular discs 219, one of which is shown at the lower end.

The top of the cylindrical shell 177 is closed by a similar end cap 180 having a side opening 182 having an integrally attached, outwardly extending clindrical boss 184 and a necked-in flanged portion 186 surrounding a central aperture. The inner wall of flange 186 engages the outer wall of a cylindrical member 221 which in turn is attached to a flat cover plate 223. As in the previous embodiments of FIGS. 1, 2, 3, and 4, a generally half cylindrical shell 35 is secured to the top surface of the cover plate 223 for directing the liquid blood and blood foam into a defoamer chamber 37.

The helically ribbed heat transfer fluid tube 225 is formed into a helical configuration and mounted in the space between the central column 211 and the inner wall of the cylindrical chamber 177 such that peripheral portions of the ribs 227 of the tube 225 advantageously contact or are in very close proximity to the exterior wall of the column 211 and the interior wall of the chamber 177.

The configuration of FIG. 8 is conveniently assembled by inserting the helically ribbed tube 225 along with the centrally located column 211 into the cylindrical shell 177. As described above with reference to the embodiments of FIGS. 1, 2, 5, 6, and 7, the shell 177 is advantageously slit along its length for facilitating insertion of the heat transfer fluid tube 225, after which the edges of the slit are bonded together. As shown, the respective heat exchanger tube ends will then extend above and below the shell 177. These ends are then inserted into the respective openings 181 and 182 formed in the upper and lower end caps 179 and 180.

A particular advantage of this construction is illustrated in FIGS. 9a and 9b. It has been found that after the helically formed tube 225 is inserted in the chamber 177, the tube 225, even when manufactured in conformance with the particular set of specifications, does not always ultimately provide an identical helical configuration. In particular, as noted above, there is a tendency on the part of the spirally formed tube 225 to uncoil such that it may be difficult to orient the tube ends along the parallel axes as illustrated in FIG. 9a. In the embodiment shown, the upper and lower end caps 179 and 180 may be oriented along non-parallel axes as shown in FIG. 9b to accommodate whatever orientation the particular heat exchanger coil 225 assumes when inserted within the chamber 177.

DETAILED DESCRIPTION OF THE PREFERRED EMBODIMENT OF FIGS. 10 THROUGH 14

The preferred embodiment of a blood oxygenator incorporating an integral heat exchanger in accordance with this invention is shown in FIGS. 10 through 14. In this embodiment, the bubble oxygenating chamber 240 is formed by a pair of mating plastic shells front shell 242 and rear shell 244. The front shell half 244 includes a grooved female peripheral flange 246, into which fits a male peripheral flange 248 on the rear shell half 242 to form a complete cylindrical shell 250. Shell halves 242 and 244 are advantageously formed by injection molding polycarbonate plastic, and may be advantageously bonded together with ethylene dichloride.

Rear shell half 244 includes a blood outlet opening 252 having an integral rearwardly extending neck 254, which is generally rectangular in cross-section. Front shell half 242 includes an upper side opening 256 and a lower side opening 258, each having an integral forwardly extending cylindrical boss 260 through which extend the respective ends of a single helically ribbed heat transfer fluid tube 262. The inside wall of these extending cylindrical bosses 260 and the proximate exterior surface of the heat exchanger tube 262 are bonded together to effect a hermetic seal. Each of the bosses 260 terminates in a tube connector 263, and redundant sealing between the bosses 260 and the heat transfer fluid tube 262 is provided by an annular sealing member 259, which may advantageously include an "O" ring (not shown).

As with the embodiment illustrated in FIGS. 3 and 4, the preferred embodiment is advantageously assembled by inserting a cylindrical extruded polycarbonate plastic interior column 264 within the helically formed ribbed tube 262. Both ends of the column 264 are hermetically sealed by end caps 265. The column 264 and the tube 262 are placed in the front shell half 242 such that the two ends of the heat exchange tube 262 extend through the openings 256 and 258. The mating shell half 244 is placed over the heat exchanger tube 262 and the mating flanges 246 and 248 are bonded together to provide a completely sealed, cylindrical shell unit 250. The peripheral portion of the ribs 266 of the tube 262 are closely proximate to and advantageously contact both the interior wall of the chamber and the exterior wall of the column 264.

The mating shells 242 and 244 are necked in at the bottom to form a hollow cylindrical neck 268. The neck 268 snugly mates with the exterior wall of a hollow, injection molded cylindrical member 270. A cylindrical layer 272 of three-dimensional, open cellular mixing material is located in the neck 268 and extends into the cylindrical member 270. The mixing material layer 272 completely fills the cross-sectional interior of the neck 268, and is supported between an upper plurality of fingers 273, extending radially inward from the inner wall of the neck 268, and a lower plurality of fingers 274 extending radially inward from the inner wall of the cylindrical member 270.

The cylindrical member 270 includes one or more blood inlet ports 276, one such port 276 being connected to the extracorporeal blood circuit by a flexible venous blood conduit (not shown).

An end cap 277 has an upwardly extending cylindrical boss 278, the exterior surface of which is bonded to the interior wall of the cylindrical member 270, thus closing off the bottom of the cylindrical member 270. A channel 279 is formed in the bottom of the end cap 278 and extends through the side thereof to form an oxygen inlet port 280 which is attached to a flexible oxygen line (not shown). The oxygen entering the inlet port 280 is caused to form a plurality of oxygen bubbles by means of a sparger 282. These bubbles flow through the venous blood entering the cylindrical member 270. The sparger 282 fills the entire cross-section of the cylindrical member 270 and rests on the upper edge of the boss 278. Alternatively, the sparger may be seated in an annular groove (not shown) in the interior wall of the cylindrical member 270. In either case, the sparger 282 is sealed around its periphery to the inner wall of the cylindrical member 270.

The venous blood and the oxygen bubbles then rise into the oxygenating chamber 240, where they contact the exterior of the tube 262. The combination of the tube ribbing 266 and the contacting surfaces of the cylinder 264 and the chamber 240 confine the flow of blood and oxygen bubbles substantially within paths of restricted area and extended length provided by the ribbing, thus providing a tortuous path for the blood and oxygen bubbles which, in combination with the mixing material layer 272, effects a thorough mixing thereof, resulting in a substantially complete transfer of oxygen into the blood and removal of carbon dioxide from the blood.

The arterialized blood, in the form of blood and blood foam, then flows out of the oxygenating chamber through the outlet opening 252 and the rectangular cross-section neck 254 into a defoamer chamber 284.

Figure 13:
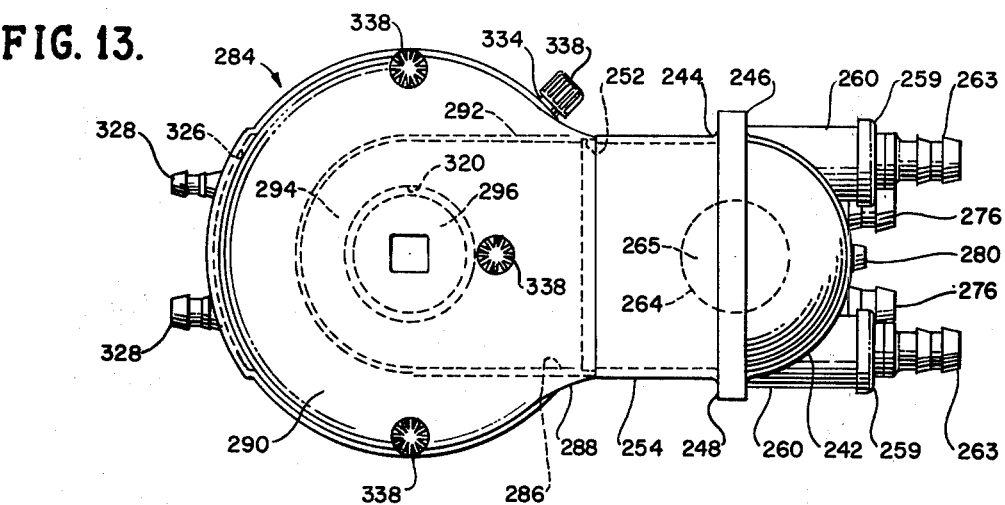
FIG. 13 is a top plan view taken along line 13—13 of FIG. 10.
Figure 14:
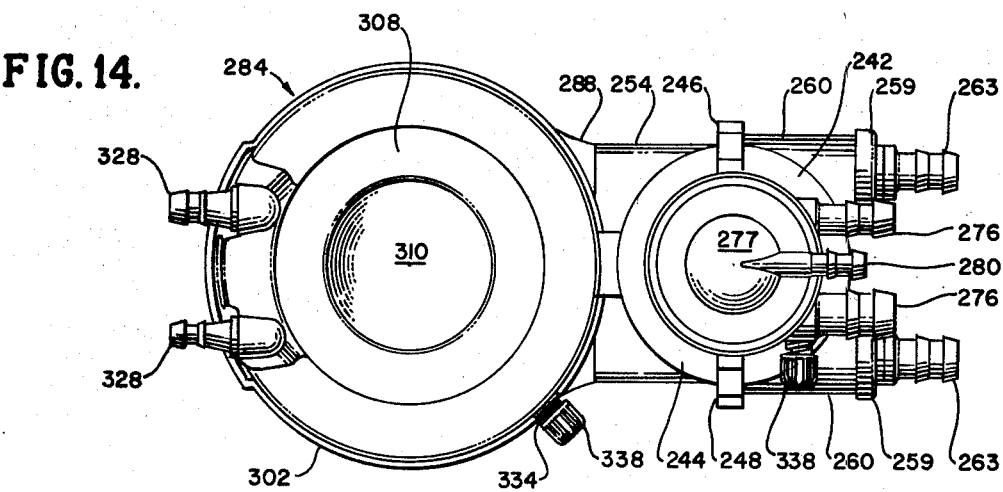
FIG. 14 is a bottom plan view taken along line 14—14 of FIG. 10.

The neck 254 communicates with a rectangular opening 286 in a rectangular cross-section boss 288 which is formed in the side of a defoamer chamber top cap 290, which is advantageously formed of injection molded polycarbonate plastic. The opening 286 in turn communicates with a fluid channel member 292 located within the top cap 290 as best shown in FIG. 13, which defines an annular defoamer inlet chamber 294.

Sealingly fixed to the underside of the top cap 290 is an extruded hollow cylindrical cascade column 296 which runs through a central axial void 298 in a tubular defoamer 300. The defoamer 300 is contained within a cylindrical injection-molded polycarbonate plastic defoamer shell 302 having an integral closed bottom, and which is bonded hermetically around its upper periphery to a downwardly extending peripheral flange 304 depending from the top cap 290. The bottom of the defoamer shell 302 includes an inner upwardly concave portion forming an annular seat 308 for a defoamer lower support member 309. At the inner periphery of the annular seat 308, the bottom of the defoamer shell 302 extends still further upwardly to form a circular, centrally raised portion 310. The support member 309 bends appropriately, so as to contact the inner surface of the raised portion 310 forming a circular centrally raised platform 311, the inner surface of which closes the bottom portion of the axial void 298 and seals the bottom of the cascade column 296.

The defoamer 300 shown is essentially as described in application Ser. No. 655,039, filed Feb. 3, 1976, to Robert M. Curtis, and assigned to the same assignee as the present application. The defoamer 300 consists of an annular tube of reticulated porous sponge material, such as polyurethane foam, and is closed in a filter cloth 312 of nylon tricot or dacron mesh. The filter cloth 312 is secured by nylon cable ties 314 to an annular upper flange 315 which extends upwardly from an annular defoamer upper support member 316, which in turn is bonded to a downwardly extending cylindrical boss 317 in the top cap 290; and a lower cylindrical flange 318 extending downwardly from the defoamer lower support member 309. Both the cloth 312 and the defoamer 300 are advantageously treated with a suitable antifoam compound.

The arterialized blood and blood foam flow from the inlet chamber 294 into the annular axial void 298 through an annular inlet 320. The majority of liquid blood entering the void 298 is guided by the column 296 to fill up the bottom of the void 298. This liquid blood flows through the defoamer 300, as generally shown by arrows 322. The blood and blood foam enter at the upper end of the defoamer 300 so that a substantial portion of the interior wall surface of the defoamer 300 is contacted by a blood foam. As a result, a substantial portion of the defoamer 300 is used to separate the blood foam from the entrapped gas such that the foam collapses and fluid blood flows into an annular reservoir 324 between the defoamer 300 and the interior wall of the defoamer chamber 284 and settles at the bottom of the chamber 284. The entrapped gas, primarily oxygen and $CO_2$, which the defoamer separates out pass out of the chamber 284 through a vent 326 located in the upper end of the chamber at the juncture of the top cap 290 and the cylindrical shell 302. As a result, only whole liquid blood collects in the reservoir 324, after having been cleaned of any particulate matter, such as blood fragments and microemboli, by the filter cloth 312. The oxygenated, filtered whole blood then passes through one or more outlet ports 328 located in the lower-most portion of the defoamer shell 302 and is returned to the patient by a flexible arterial conduit (not shown)..

The defoamer chamber 284 advantageously includes externally applied indicia 330 of the volume of blood contained therein. The oxygenator may also include an externally threaded venous blood sampling port 332 proximate the venous blood inlet 276, and an arterial blood sampling port 334 in the lower portion of the defoamer chamber 284. One or more priming ports 336 may also be provided in the top cap 290. The ports 332, 334, and 336 are conveniently sealed by screw caps 338.

By way of specific example, an adult blood oxygenator with and integral heat exchanger has been constructed in accordance with the perferred embodiment shown in FIGS. 10 through 14. The oxygenating chamber 240 has an inside diameter of approximately three inches, while the hollow central column 264 in the oxygenating chamber has an outside diameter of approximately 1.625 inches. The aluminum tubing used to form the heat exchanger tube 262 has an outside diameter of $\frac{3}{4}$ inch, which, when twisted to form the helical rib 266, yields and outside diameter of aproximately 0.65 inches from ridge to ridge of the ribbing and approximately $\frac{1}{2}$ inch from groove to groove between the ribbing. The wall thickness of the tube is approximately 0.016 inches. The hard anodized coating adds approximately 0.002 inches to the outside diameter measurements and 0.001 inches to the wall thickness. When fully assembled, with the central column 264 and the heat exchange tube 262 in place, the oxygenating chamber 240 has a capacity of approximately 450 milliliters.

A still smaller capacity oxygenating chamber employing an anodized heat exchange tube is disclosed in co-pending application Ser. No. 863,989 filed Dec. 23, 1977.

DETAILED DESCRIPTION OF THE ADVANTAGES OF THE INVENTION

Heat exchangers constructed in accordance with this invention offer significant advangtages for use in extracorporeal blood circuits.

One such advantage is a highly efficient transfer of heat from the blood to the heat transfer fluid. This is of substantial importance since the quicker the patient's blood is cooled and rewarmed, the shorter the time the patient has to be connected to the bypass extracorporeal blood circuit.

The efficiency of a heat exchanger normally expressed as a performance factor P/F in accordance with the following equation:

$$P/F = \frac{\text{Temperature Blood Out} - \text{Temperature Blood In}}{\text{Temperature } H_2O \text{ In} - \text{Temperature Blood In}}$$

Heat exchangers constructed in accordance with this invention and integral within a blood oxygenator as in the preferred embodiment of FIGS. 10 through 14 consistently achieved excellent performance factors when functionally tested in vitro. A series of in vitro tests conducted in May and July, 1977 produced performance factors ranging from 0.681 to 0.698 for a blood flow rate of two liters/minute and from 0.413 to 0.421 for a blood flow rate of six liters/minute. Although early tests of units employing a polyurethane-coated fluted aluminum heat transfer fluid tube (as described in the parent co-pending application, Ser. No. 685,020, filed May 10, 1976) showed performance factors of this order, it has been found that the performance factors of production units using a polyurethane-coated tube are measurably lower, although still excellent as compared with prior art heart exchangers for extracorporeal blood circuits. Thus, production units employing polyurethane-coated hollow fluted tubes in the same series of in vitro tests conducted in May and July, 1977 and under the same conditions, displayed performance factors ranging from 0.503 to 0.528 for a blood flow rate of two liters/minute and from 0.272 to 0.275 for a blood flow rate of six liters/minute.

The enhanced and consistent heat exchange performance of the units embodying the anodized heat transfer fluid tube is attributed to the greater thermal conductivity of the hard anodized coating.

A number of factors contribute to the excellent heat transfer efficiency of the present invention and include the following:

1. The combination of the flutes of the heat transfer fluid tube and proximate inner and outer surface walls of the blood chamber provides a plurality of continuous, restricted area flow paths offering substantially uniform flow impedance to the blood and blood foam. As a result, the blood and blood foam have a long residence time in the heat exchanger. Moreover, this structure avoids areas of stagnation which otherwise hinder heat transfer from the blood and are also undesirable from a physiological standpoint. In the tests conducted to date on the embodiments of FIGS. 3, 4, and 8 through 14, the blood and blood foam was observed to be in constant circulation through these restricted flow paths and having extensive contact with and long residence time with the heat exchanger tube. Only minimal areas of stagnation were evident.

2. The extensive helical hollow ribs of the heat transfer fluid tube provide a substantial surface area for transferring heat from the heat transfer fluid to the blood and blood foam. The tubes used in the above-described embodiments typically have an external surface area of the order of 200 to 300 square inches.

3. Although the direction of fluid flow through the heat exchanger tube may be in either direction, the heat transfer performance is optimized by operating as a counterflow exchanger, i.e., in the manner described above wherein the blood and heat transfer fluid flow in generally opposite directions.

4. The wall thickness of the helically ribbed tube may be relatively thin, e.g., 0.016 in., so as to further improve its heat transfer properties. The anodized aluminum tubes have a high thermal conductivity.

5. The hollow ribbed heat exchanger tube has a sufficiently large average internal diameter, e.g., approximately 0.5 inch, for providing a high rate of flow of the heat transfer fluid, e.g. 21 liter/minute of water.

In addition to providing a highly efficient heat exchanger, the helically ribbed heat exchanger tube in combination with the inner and outer wall surfaces of the blood chamber has been found to contribute to the oxygenation process. Thus, the blood and blood foam mixture emerging from the top of the three-dimensional mixing material in the embodiments of FIGS. 1, 2, 3, 4, 8, 9a and 9b and 10 through 14, is subjected to additional oxygen transfer to the blood and carbon dioxide removal from the blood by virtue of the lengthy paths of restricted cross-sectional area through which the blood and blood foam pass through the heat exchanger. Tests conducted to date indicate for example that in the blood oxygenators of FIGS. 3, 4, 8, 9, and 10 - 14, a one-inch thick by two-inch diameter cylinder of mixing material in combination with the heat exchanger accomplishes approximately the same blood-gas interchange as a two-inch thick by three-inch diameter cylinder of foam without the integral heat exchanger incorporated in the blood chamber.

Further, the copending application, Ser. No. 863,989 filed Dec. 23, 1977 disclosed and claims a blood oxygenator in which substantially all the mixing of the blood and oxygen is provided by a hollow ribbed heat exchanger tube in combination with the wall surfaces.

Although the integral heat exchanger embodiments described above have incorporated the heat exchanger within the oxygenation chamber, it will be apparent to those knowledgeable in the art that the significant features of the heat exchanger tube which contribute to its high heat transfer efficiency will be beneficial in other locations within the blood oxygenator. Thus by way of specific example, the helically ribbed heat transfer fluid tube may be located within the defoamer column such that the blood flowing within or through the defoamer member is caused to circulate through the flutes of the heat exchanger tube.

The integral nature of the heat exchanger tube also provides an important advantage in providing an effective seal for preventing any possible contamination of the blood by the heat transfer fluid. Thus, in the present invention, the heat exchanger tube is advantageously constructed as a continuous member with no connections being made to the tube within the blood chamber. Any leak at the connection of the heat exchanger tube and the flexible water or other heat transfer fluid conduit will merely leak water or other fluid external of the blood chamber.

In addition, the thickness of the heat exchanger tube, after formed into a ribbed configuration, is ample to handle fluid pressures considerably higher than those encountered in clinical practice. This is important since typically the heat exchanger tube is connected directly to a water faucet in the operating room which, turned full on, may deliver water at a pressure as high as 60 psi. Inadvertent closing of the drain discharge can then build up pressure within the heat exchanger to 60 psi. Such high pressures can rupture certain prior art heat exchanger configurations concurrently in extensive use in extracorporeal blood circuits. In contrast, in the present invention, the ribbed tubes have been tested at substantially high pressures, i.e., 120 psi without any indication of structural damage or rupture.

In addition to its excellent heat transfer characteristics, the present invention is efficiently and economically manufactured. Thus, the helically ribbed tube is an integral unit which may be completely tested for leaks before and/or after assembly into the blood carrying chamber.

What is claimed is:

1. A blood oxygenator having an integral heat exchanger for regulating the temperature of the blood flowing in an extracorporeal blood circuit, comprising:
   an oxygenating chamber;
   first means for introducing blood and bubbles of oxygen into said oxygenating chamber for forming blood foam within said chamber; and
   second means for both (a) contributing to the transfer of oxygen into the blood and the removal of carbon dioxide from the blood, and (b) simultaneously regulating the temperature of said blood, said second means comprising:
   a heat transfer fluid conduit substantially entirely composed of highly thermal conductive, blood compatible material, and including heat exchange fluid inlet and outlet means, and having rib means disposed along its length for providing a blood flow passage considerably longer than the length of said fluid conduit, said rib means being located in contact with or closely proximate to the inner wall of said oxygenating chamber so that substantially all of said blood and blood foam produced by said first means flows in contact with the external surfaces of said heat transfer fluid conduit through a plurality of restricted area, extended length flow paths around the exterior of the heat transfer fluid conduit provided by said blood flow passage in combination with said inner wall prior to any substantial defoaming of the blood foam and with minimal areas of stagnation for said blood and blood foam with a resulting long residence time of blood and blood foam in contact with said heat transfer fluid conduit.

2. The blood oxygenator having an integral heat exchanger of claim 1, wherein said rib means is a continuous hollow helical rib providing a continuous helical flute passage.

3. The blood oxygenator having an integral heat exchanger of claim 1, wherein said heat transfer fluid conduit is a continuous length of metal tubing whose exterior surface is substantially entirely electrolytically oxidized to form a hard anodized coating thereon.

4. The blood oxygenator having an integral heat exchanger of claim 3, wherein said heat transfer fluid conduit is a continuous length of formed aluminum tubing whose exterior surface is substantially entirely electrolytically oxidized to form a hard anodized coating thereon.

5. A blood oxygenator having an integral heat exchanger for regulating the temperature of the blood flowing in an extracorporeal blood circuit comprising:
an oxygenating chamber;
first means for introducing blood and bubbles of oxygen into said oxygenating chamber for forming blood foam within said chamber; and
second means for both (a) contributing to the transfer of oxygen into the blood and removing carbon dioxide from the blood and (b) simultaneously regulating the temperature of said blood, said second means comprising:
a heat transfer fluid conduit having anodized external surfaces and including heat exchange fluid inlet and outlet means and having a substantially continuous hollow helical rib along its length providing a continuous helical flute passage considerably longer than the length of said fluid conduit, said helical rib being located in contact with or closely proximate to wall means in said oxygenating chamber so that substantially all of said blood and blood foam produced by said first means flows in contact with said anodized external surfaces of said heat transfer fluid conduit through a plurality of restricted area, extended length flow paths around the exterior of the heat transfer fluid conduit provided by said helical flute passage in combination with said walls means prior to any substantial defoaming of the blood foam and with minimal areas of stagnation for said blood and blood foam with a resulting long residence time of the blood and blood foam in contact with said heat transfer fluid conduit.

6. The blood oxygenator having an integral heat exchanger of claim 5 wherein said heat transfer fluid conduit is a continuous length of formed aluminum tubing whose substantially entire exterior surface is electrolytically oxidized to form a hard anodized coating thereon.

7. The blood oxygenator having an integral heat exchanger of claim 6 wherein said heat transfer fluid conduit has an overall helical configuration.

8. The blood oxygenator having an integral heat exchanger of claim 7 wherein said wall means includes the interior wall of said oxygenating chamber and the exterior wall of a centrally located cylindrical column located within said chamber, said helically configured heat transfer fluid conduit being located between said column and said interior wall of said chamber so that said exterior wall of said column is located in contact with or closely proximate to peripheral portions of said hollow rib means.

9. A blood oxygenator having an integral heat exchanger comprising:
an oxygenating chamber;
means for introducing blood and bubbles of oxygen into said oxygenator chamber for forming blood foam;
means for (a) contributing to the transfer of oxygen into the blood and removal of carbon dioxide from the blood and (b) simultaneously regulating the temperature of said blood, said means comprising:
an aluminum heat transfer tube whose substantially entire exterior surface is electrolytically oxidized to form a hard anodized coating thereon, said tube including heat exchange fluid inlet and outlet means and having an integral, substantially continuous hollow helical rib along its length providing a substantially continuous helical flute passage considerably longer than the length of said tube, said tube having an overall helical configuration with peripheral portions of said rib in contact with or closely proximate to a wall of said oxygenating chamber so that substantially all of said blood and blood foam flows in contact with external surfaces of said heat transfer tube through a plurality of flow paths of restricted area and extended length around the exterior of said tube prior to any substantial defoaming of the blood foam, said flow paths being provided with minimal areas of stagnation for said blood and blood foam and formed by said helical flute passage in combination with a wall of said oxygenating chamber for achieving long residence time of the blood and blood foam in contact with said heat transfer tube.

* * * * *

UNITED STATES PATENT AND TRADEMARK OFFICE
CERTIFICATE OF CORRECTION

PATENT NO. : 4,138,464
DATED : Feb. 6, 1979
INVENTOR(S) : John E. Lewin

It is certified that error appears in the above-identified patent and that said Letters Patent are hereby corrected as shown below:

Column 1, line 68, after "has" change "ofter" to --often--.
Column 5, line 13, after "provides" change "and" to --an--.
Column 5, line 21, after "shell" change "and" to --are--.
Column 6, line 2, after "the" change "heat" to --heating--.
Column 12, line 38, after "art" change "heart" to --heat--.

Signed and Sealed this

Twentieth Day of November 1979

[SEAL]

Attest:

RUTH C. MASON
Attesting Officer

LUTRELLE F. PARKER
Acting Commissioner of Patents and Trademarks